US012797572B2

(12) United States Patent
Boulanger et al.

(10) Patent No.: US 12,797,572 B2
(45) Date of Patent: *Nov. 17, 2026

(54) GAS SUPPLY INSTALLATION COMPRISING A MEDICAL VENTILATOR AND AN NO DELIVERY DEVICE WITH AN EMERGENCY DOSING SYSTEM

(71) Applicant: INOSYSTEMS, Antony (FR)

(72) Inventors: Thierry Boulanger, Antony (FR); Frederic Marchal, Antony (FR); Mary Schmitt, Bagneaux (FR)

(73) Assignee: INOSYSTEMS, Antony (FR)

(*) Notice: Subject to any disclaimer, the term of this patent is extended or adjusted under 35 U.S.C. 154(b) by 640 days.

This patent is subject to a terminal disclaimer.

(21) Appl. No.: 18/225,483

(22) Filed: Jul. 24, 2023

(65) Prior Publication Data

US 2024/0050686 A1 Feb. 15, 2024

(30) Foreign Application Priority Data

Aug. 11, 2022 (FR) ....................................... 2208243

(51) Int. Cl.
*A61M 16/12* (2006.01)
*A61M 16/00* (2006.01)
(Continued)

(52) U.S. Cl.
CPC .......... *A61M 16/12* (2013.01); *A61M 16/203* (2014.02); *G05D 7/0676* (2013.01);
(Continued)

(58) Field of Classification Search
CPC ............ A61M 16/0051; A61M 16/024; A61M 16/10; A61M 16/12; A61M 16/122;
(Continued)

(56) References Cited

U.S. PATENT DOCUMENTS 12,576,233 B2 * 3/2026 Boulanger .......... A61M 16/024
2005/0172966 A1 * 8/2005 Blaise ................. A61M 16/202 128/204.21

(Continued)

FOREIGN PATENT DOCUMENTS

EP 2522384 A1 * 11/2012 ............. A61B 5/082
EP 3888727 A1 10/2021

(Continued)

OTHER PUBLICATIONS

Machine translation of EP-2522384-A1.*
Search Report from corresponding application FR2208243 dated Mar. 16, 2023.

*Primary Examiner* — Joseph D. Boecker
(74) *Attorney, Agent, or Firm* — Quantum Patent Law Firm; Seongyoune Kang

(57) ABSTRACT

An installation for supplying gas to a patient, comprises an NO delivery device, an NO injection line with a valve device, a backup line that connects to the injection line and comprises a backup solenoid valve and a flow rate control device, and control means; and a medical ventilator that supplies a respiratory gas to a patient circuit to which the NO delivery device is connected. A flow rate sensor supplies the control means with a measurement signal of the gas flow rate in the patient circuit. In the event of interruption of reception of the measurement signal, the backup solenoid valve switches to an open position, the valve device switches to a closed position and the flow rate control device supplies the $NO/N_2$ mixture at a pre-regulated backup flow rate, determined on the basis of the measurement signal supplied by the flow rate sensor, before said interruption.

17 Claims, 5 Drawing Sheets

(51) Int. Cl.
*A61M 16/20* (2006.01)
*G05D 7/06* (2006.01)

(52) U.S. Cl.
CPC ............... *A61M 2016/0033* (2013.01); *A61M 2202/0208* (2013.01); *A61M 2202/0275* (2013.01); *A61M 2205/50* (2013.01); *A61M 2205/70* (2013.01)

(58) Field of Classification Search
CPC .............. A61M 16/125; A61M 16/202; A61M 16/203; A61M 16/204; A61M 2202/0275; A61M 2205/16; A61M 2205/3334; A61M 2016/0027; A61M 2016/0039; A61M 2016/102
See application file for complete search history.

(56) References Cited

U.S. PATENT DOCUMENTS

| | | | | |
|---|---|---|---|---|
| 2017/0348503 | A1* | 12/2017 | Westermark ........ | A61M 16/024 |
| 2021/0308411 | A1* | 10/2021 | Boulanger ............ | A61M 16/12 |
| 2025/0213812 | A1* | 7/2025 | Boulanger ............ | A61M 16/12 |

FOREIGN PATENT DOCUMENTS

| | | | | | |
|---|---|---|---|---|---|
| FR | 3131538 | A1 * | 7/2023 | ............ | A61M 16/12 |
| WO | 2016096056 | A1 | 6/2016 | | |

* cited by examiner

GAS SUPPLY INSTALLATION COMPRISING A MEDICAL VENTILATOR AND AN NO DELIVERY DEVICE WITH AN EMERGENCY DOSING SYSTEM

CROSS-REFERENCE TO RELATED APPLICATION

This application claims priority to FR2208243, filed Aug. 11, 2022, and the entire contents of which are incorporated herein by reference.

BACKGROUND

The invention relates to a gas supply installation comprising a medical ventilator, that is, a medical apparatus for administering gas, and a device or apparatus for delivering gaseous nitric oxide (NO) in order to supply a gas containing NO to a patient, via a main NO delivery system, which installation further comprises an NO emergency dosing system making it possible to supply the gas containing NO at a given backup flow rate in the event of the malfunction of the main NO delivery system, in particular in the event of the loss of the signal coming from the flow rate sensor arranged on the patient circuit supplied by the medical ventilator.

NO is a gas which, when inhaled, dilates the pulmonary vessels and increases oxygenation by improving gas exchange. The properties of NO are used to treat various medical conditions such as persistent pulmonary hypertension of the newborn (PPHN), acute respiratory distress syndrome (ARDS) observed mainly in adults, or pulmonary hypertension in heart surgery, as disclosed in particular by EP-A-560928, EP-A-1516639 or U.S. Pat. No. 10,201,564.

Usually, a small quantity of gaseous NO (i.e. a few ppm by volume), diluted in nitrogen (N2), is injected into a gas flow containing at least 21% by volume of oxygen (O2), which is then inhaled by the patient. The concentration of NO, which corresponds to a dosage, is determined by the physician or similar. Typically, the gas containing oxygen is usually a mixture of N2/O2 or air, such as medical-grade air. Generally, the concentration or dosage of NO in the gas inhaled by the patient, that is, after the NO/N2 mixture has been mixed with the air or an O2/N2 mixture, is between 1 and 80 ppm by volume (ppmv), depending on the population treated, i.e. newborns or adults, and therefore the disease to be treated.

The gas inhaled by the patient can be delivered by way of an NO delivery device associated with a mechanical ventilator, as is described by U.S. Pat. No. 5,558,083. The NO delivery device is fluidly connected to one or more gas cylinders containing an N2/NO mixture, the NO concentration of which is typically between 200 and 800 ppmv. Generally, the NO delivery system comprises an NO injection module placed in the inhalation branch of a patient circuit connected fluidly, on the one hand, to the mechanical ventilator and, on the other hand, to a respiratory interface delivering the NO-enriched gas to the patient, for example a breathing mask, a tracheal intubation tube or similar.

An NO delivery installation also comprises a flow rate sensor that measures the gas flow rate delivered by the mechanical ventilator (i.e. air or N2/O2 mixture) into the patient circuit in order to determine the quantity of NO to be delivered in order to satisfy the dosage set by the physician. It must be noted that this so-called “flow rate” sensor can be of the type that measures and supplies flow rate signals or measurements per se, but also of the type that measures and supplies pressure signals or measurements that are then converted into a flow rate by control means, in particular in a microprocessor.

The NO dosage can be provided by way of a proportional solenoid valve that delivers a continuous flow of NO-containing gas and is associated with a flow rate sensor, referred to as the NO flow rate sensor, these two components being arranged in the NO delivery device, and by an injection line that connects the NO delivery device to the NO injection module arranged on the patient circuit, as described in U.S. Pat. No. 5,558,083.

Other NO delivery devices exist, in which the proportional solenoid valve is replaced by a plurality of “all-or-nothing” solenoid valves, delivering the gas intermittently, that is in the form of pulses, generally at a high frequency, the amplitude and duration of which guarantee the correct quantity of gas circulating in the injection line connected to the NO injection module.

In any event, the known NO delivery installations receive the measurements or signals from the flow rate sensor placed in the inhalation branch of the patient circuit and adjust in real time the quantity of NO to be delivered, according to the desired dosage, by controlling the flow of NO in the injection line. The association of the flow rate sensor placed in the inhalation branch of the patient circuit and the proportional or “all-or-nothing” solenoid valve(s) and the NO flow rate sensor, if present, together with the control means as described below, which are arranged in the NO delivery device, form a main NO delivery system.

Since NO is a therapeutically effective agent, that is, very low concentrations (i.e. a few ppmv) produce a therapeutic effect, its correct dosing is of critical importance, and medical personnel must constantly adjust the dosage according to the condition of the patient. As a result, when the condition of the patient changes, the NO concentration must be gradually reduced or, conversely, increased in order to take into account the condition of the patient. For example, in a situation of withdrawal from a newborn whose condition is improving, it is customary to gradually reduce the dosage, for example in steps of 1 ppm, until a zero value is reached, making it possible then to stop NO delivery. Gradual reduction of the NO concentration makes it possible to avoid a “rebound effect”, which can occur in cases of rapid variation of the concentration, typically in cases of abrupt discontinuation of the treatment, which could seriously worsen the condition of the patient.

NO delivery installations are sophisticated electromedical systems that are susceptible to faults or malfunctions that can have a considerable impact on the therapy being provided. For example, an electronic malfunction or fault, in particular of the control means and/or of the main NO delivery system, can cause the apparatus to fail and therefore NO delivery to stop completely, with the negative consequences mentioned above.

There are multiple possible failures, such as for example:

- the loss of the signal coming from the flow rate sensor measuring the gas flow rate delivered by the mechanical ventilator, which flow rate sensor is arranged in the patient circuit of the ventilator and subject to multiple stresses from users;
- a loss of electrical connection between the solenoid valve(s) or the NO flow rate sensor and the control means, due to repeated vibrations occurring for example when a patient is being transported; or
- the abrupt loss of the control means in the event of a major failure, originating from an electronic malfunction or fault, for example.

Under such circumstances, the NO delivery device must alert the user, by means of an audible and/or visual alarm signal, that prompt action is required, for example to switch to a backup pneumatic injection mode so as to limit as far as possible the undesirable effects associated with the discontinuation of the therapy caused by the failure.

This switching to backup mode is usually done by manually actuating a rotary knob or similar that commands the change-over from the normal NO administration mode to a backup mode in which there is, for example, continuous delivery of a fixed flow rate of N2/NO mixture, i.e. of the order of 250 ml/min. Such a backup dosing mechanism or system is not without risk, in particular for the following reasons:

- its activation requires the presence of a person who is authorized to take this action, for example a neonatologist. Several minutes can thus go by before this person arrives and therefore before the backup dose is established, which results in the discontinuation of the therapy and exposes the patient to a rebound effect;
- the backup dose, i.e. a single flow rate of N2/NO mixture, cannot guarantee that the desired dosage is satisfied. In particular, when the backup dose is much below the desired dosage, the patient can be exposed to an abrupt change of concentration and can potentially be subject to considerable adverse effects; and/or
- the backup dose is incompatible with some types of ventilator delivering very low volumes, such as high-frequency oscillation (HFO) ventilators, since it can result in an inhaled NO concentration that is too high and can reach levels that are dangerous to the patient. Therefore, when the patient is being treated with such a ventilator (i.e. an HFO ventilator), there is no way to administer the NO to the patient, which results in the aforementioned risks associated with the abrupt stoppage of treatment.

It therefore appears that the current backup dosing mechanisms cannot guarantee a satisfactory level of safety and that it would be desirable for the patient, in the event that a backup dose is applied due to malfunction of the NO delivery installation, to be able to maintain NO therapy without interrupting the therapy and without worrying about the type of ventilator, i.e. an HFO or other ventilator, with which the NO delivery system of the NO delivery installation interacts.

In an effort to overcome this, EP-A-3410927 proposes a dosage in response to the loss of the signal, i.e. the data, coming from the flow rate sensor measuring the gas flow rate delivered by the mechanical ventilator, which flow rate sensor is arranged in the patient circuit of the ventilator and subject to multiple stresses from users. The proposed solution relies on operating the proportional solenoid valve of the NO delivery device so as to deliver a constant NO flow rate based on stored historical data previously measured by the flow rate sensor measuring the gas flow rate delivered by the ventilator and stored in a memory of the apparatus.

However, this solution is flawed as it does not make it possible to ensure the delivery of an average NO flow rate in the event of a different type of failure, such as the loss of electrical connection with the solenoid valve(s), or between the NO flow rate sensor and the control means, or even the abrupt loss of the control means themselves.

In other words, one problem is being able to maintain a dosage, that is, the treatment of the patient using NO inhaled at the desired concentration, in the event of the failure or malfunction of the flow rate sensor, which is typically situated in the patient circuit and to which the medical ventilator and the NO delivery device are connected, but also in the event of the other failures mentioned above.

SUMMARY

One solution according to the invention relates to an installation for supplying gas to a patient, comprising:

- an NO delivery (i.e. NO supply) device or apparatus configured to supply an NO/N2 gas mixture, comprising:
- an NO injection line for conveying the NO/N2 gas mixture,
- a valve device arranged on the injection line in order to control the circulation of the NO/N2 gas mixture in the injection line,
- a backup line that connects fluidly to the injection line upstream and downstream of the valve device, said backup line comprising a backup solenoid valve and a flow rate control device, and
- control means, also referred to as an operating unit, configured to interact with the backup solenoid valve, the flow rate control device and the valve device,
- a medical ventilator configured to supply a respiratory gas containing oxygen, typically approximately at least 21% oxygen, such as air or an N2/O2 mixture,
- a patient circuit to which the NO delivery device and the medical ventilator are fluidly connected in order to supply said patient circuit with said NO/N2 gas mixture and with said respiratory gas containing oxygen, typically approximately at least 21% oxygen, and
- a flow rate sensor configured to determine (i.e. measure) and supply to the control means of the NO delivery device at least one measurement signal representing the gas flow rate within the patient circuit, namely one or more flow rate or pressure measurement signal(s).

In addition, according to the invention, in the event of the interruption of the reception by the control means of the NO delivery device or apparatus, that is, the loss of the measurement signal supplied by the flow rate sensor:

- the backup solenoid valve switches, i.e. is configured to switch, to an open position in order to allow the circulation of the NO/N2 gas mixture in the backup line,
- the valve device switches, i.e. is configured to switch, to a closed position in order to stop any circulation of gas in the injection line, and
- the flow rate control device is configured to supply the NO/N2 gas mixture at a pre-set, i.e. pre-regulated, backup gas flow rate, where said backup gas flow rate is determined by the control means on the basis of at least one measurement signal supplied by the flow rate sensor, before said interruption of reception of said signal, and pre-regulated by a command to the flow rate control device from said control means, before said interruption of reception of said signal.

In the context of the invention:

- "ppmv" means parts per million by volume.
- "% vol." means percentage by volume.
- "NO" denotes nitric oxide.
- "N2" denotes nitrogen.
- "O2" denotes oxygen.
- "Normal operation" is given to mean usual operation, without any breakdown, malfunction, fault or similar.
- "Malfunction" is given to mean a breakdown, a fault, a disconnection or similar, reversible or permanent, of electrical, mechanical or any other origin, affecting normal operation by preventing any reception by the control means of the signal(s) measured (i.e. the measurements taken) and transmitted by the flow rate sensor.

"Flow rate sensor" is given to mean a sensor of the type that measures and supplies one or more flow rate signal(s) or measurement(s) per se, or of the type that measures and supplies one or more pressure signal(s) or measurement(s) that are then converted into a flow rate by the control means.

According to the embodiment in question, the NO supply device or apparatus and/or the installation of the invention can comprise one or more of the following features:

the valve device of the NO delivery device is configured so that it is normally in a closed position (i.e. idle state) in order to prevent, i.e. stop or oppose, any circulation of gas in the injection line, that is, the closed position corresponds to its idle state.

the backup solenoid valve of the NO delivery device is configured so that it is normally in an open position (i.e. idle state) in order to allow, i.e. permit, the circulation of gas in the backup line, that is, the open position corresponds to its idle state.

in their idle state, the valve device and the backup solenoid valve of the NO delivery device are no longer or not commanded by the control means.

in the event of a loss of signal, the control means are configured to stop operating (i.e. no longer command) the valve device and the backup solenoid valve of the NO delivery device, which then automatically switch to their idle state.

in the event of a loss of signal, the control means are configured to stop operating (i.e. no longer command) the valve device and the backup solenoid valve of the NO delivery device so that:

said valve device switches from an open position permitting the passage of gas in the injection line to the closed position and said backup solenoid valve switches from a closed position preventing the passage of gas in the backup line to the open position.

a flow rate measurement device is arranged on the injection line of the NO delivery device in order to take one or more measurements of the flow rate of the NO-containing gas circulating in the injection line.

the backup line is fluidly connected to the injection line upstream or downstream of the flow rate control device.

the control means (i.e. operating device) are further configured to calculate the backup gas flow rate (i.e. backup NO/N2 mixture flow rate) on the basis of the last gas flow rate measured by the flow rate sensor measuring the gas flow rate coming from the ventilator, before said interruption of reception of said signal.

the control means are further configured to determine, i.e. calculate, the backup flow rate on the basis of one or more respiratory gas flow rates, preferably a plurality of gas flow rates, supplied by the ventilator having been measured by the flow rate sensor, before said interruption of reception of said signal, and on the basis of a desired dosage, that is a final NO concentration to be obtained after the mixing of the NO/nitrogen mixture coming from the NO delivery device and the respiratory gas flow containing at least 21% oxygen coming from the ventilator, typically air or an oxygen/nitrogen mixture.

the flow rate control device is configured to supply the NO/N2 gas mixture at a pre-set backup gas flow rate, determined by the control means on the basis of a plurality of measurement signals supplied by the flow rate sensor in a given duration, before said interruption of reception of said signal, for example in several seconds or tens of seconds, said measurement signals being used to calculate an average flow rate over said given duration.

the backup gas flow rate is determined by the control means on the basis of an average gas flow rate calculated on the basis of a plurality of gas flow rates measured by the flow rate sensor in a given duration, before said interruption of reception of said signal; the given duration is preferably between several seconds and several tens of seconds.

the control means are configured to determine, i.e. calculate, the backup flow rate on the basis of one or preferably a plurality of respiratory gas flow rates supplied by the ventilator having been measured by the flow rate sensor, before said interruption of reception of said signal, and a desired dosage at which the NO content of the mixture administered to the patient is between 1 and 80 ppmv.

the control means of the NO delivery device are further configured to, during normal operation (i.e. before any malfunction), command the backup solenoid valve so that it is in a closed position (i.e. active state) preventing any circulation of gas in the backup line.

the control means of the NO delivery device are further configured to, during normal operation, command the valve device to permit (i.e. active state) the circulation of gas in the injection line and at least one gas flow rate measurement by the flow rate measurement device.

the control means are further configured to, before any malfunction with loss of signal coming from the flow rate sensor (i.e. during normal operation), control the flow rate control device of the backup line to pre-regulate the backup gas flow rate to be delivered in the event of the interruption of the reception of the signal from the flow rate sensor, that is, in the event of a loss of signal from the flow rate sensor.

during normal operation, the flow rate sensor is configured to take a plurality of flow rate or pressure measurements (i.e. of the respiratory gas supplied by the ventilator) and transmit said flow rate or pressure measurement(s) to the control means, preferably via a differential pressure sensor.

during normal operation, the control means are further configured to determine, i.e. calculate, an average gas flow rate in a given duration on the basis of a plurality of flow rate or pressure signals or measurements taken by the flow rate sensor (i.e. of the respiratory gas supplied by the ventilator), that is the respiratory gas flow rate supplied by the ventilator averaged over the given duration, for example over several seconds or tens of seconds.

the average flow rate is calculated by the control means over a given duration of several seconds to several tens of seconds, typically between 5 and 60 seconds, or another duration.

the control means are further configured to store at least one gas flow rate (i.e. of the respiratory gas supplied by the ventilator), in particular the average flow rate, determined on the basis of the flow rate or pressure signal(s) or measurement(s) coming from the flow rate sensor (i.e. of the respiratory gas supplied by the ventilator).

the respiratory gas containing oxygen supplied by the ventilator is air or a nitrogen/air mixture containing at least 21% by volume of oxygen, or even pure oxygen (i.e. approximately 100% by volume).

it comprises storage means.

the flow rate values obtained via the flow rate sensor are stored in the storage means of the NO delivery device.

the storage means comprise a computer memory, for example a random access memory.

the patient circuit comprises an NO injection module supplied with an NO/N2 mixture by the NO delivery device, preferably via the injection line, such as a flexible gas duct.

the flow rate sensor is arranged on the patient circuit, preferably on an inhalation branch of said patient circuit, and is electrically connected to the control means, via one or more electrical connections (e.g. cables or similar).

the flow rate sensor (i.e. used to measure the respiratory gas flow rate supplied by the ventilator) is arranged on the patient circuit between the medical ventilator and the NO injection module.

according to one embodiment, the flow rate sensor is a mass flow sensor or similar. In this case, the flow rate sensor is electrically connected to the control means, via one or more electrical connections such as cables or similar.

according to another embodiment, the flow rate sensor is of the type that measures differential pressure, that is a pressure sensor. In this case, the flow rate sensor is arranged on the patient circuit and interacts with a differential pressure sensor arranged in the NO delivery apparatus.

the differential pressure sensor is arranged on a circuit board in the NO delivery apparatus and interacts with the control means of the NO delivery apparatus; a single circuit board preferably bears said differential pressure sensor and at least one microprocessor of said control means.

the flow rate sensor comprises a pressure measurement module arranged on the patient circuit, in particular in the inhalation branch, comprising pressure measurement ports.

the measurement module is traversed by the gas flow circulating in the patient circuit, in particular in the inhalation branch.

the pressure measurement ports of the measurement module of the flow rate sensor situated on the patient circuit are pneumatically connected to the differential pressure sensor by an upstream line and a downstream line for measuring pressure in order to supply gas pressures to said differential pressure sensor. Preferably, the upstream line and the downstream line are gas ducts, pipes or similar.

the interruption of the reception, by the control means of the NO delivery device, of said at least one measurement signal supplied by the flow rate sensor results from, i.e. follows, the inadvertent disconnection of at least one of the upstream and downstream pressure measurement lines.

the pressure measurement module of the flow rate sensor comprises an internal gas passage comprising an internal restriction creating a pressure drop, i.e. causing a pressure differential or gradient, when a gas flow circulates in the internal passage and passes through said internal restriction.

the pressure measurement module of the flow rate sensor comprises upstream and downstream chambers, within the internal passage of the flow rate sensor, separated by a wall traversed by a gas passage orifice so as to form the internal restriction.

the upstream and downstream pressure measurement lines fluidly connect the pressure measurement module of the flow rate sensor to the differential pressure sensor so as to make it possible to measure the pressure before and after the pressure drop, that is, upstream and downstream of the internal restriction.

the upstream and downstream pressure measurement lines are fluidly connected to the upstream and downstream chambers of the pressure measurement module of the flow rate sensor in order to take measurements of the pressure of the circulating flow, that is before and after the pressure drop.

the upstream and downstream pressure measurement lines comprise pressure measurement ducts or similar configured to supply the differential pressure sensor with the pressures measured before and after the pressure drop.

the differential pressure sensor is arranged in the NO delivery device.

the differential pressure sensor is electrically connected to the control means or is configured to transmit the pressure measurements coming from the flow rate sensor to the control means.

the control means are configured to computer process the pressure measurements, i.e. the pressure differential, and deduce at least one gas flow rate therefrom.

the control means are configured to determine at least one respiratory gas flow rate coming from the ventilator and circulating in the inhalation branch on the basis of the pressure values and at least one pre-recorded lookup table making it possible to convert a (the) pressure value(s), in particular transmitted by the differential pressure sensor, into a flow rate value.

the pre-recorded lookup table(s) is/are recorded in the storage means.

the differential pressure sensor is arranged in the NO delivery device and interacts with the control means in order to supply them with the pressure values measured by the measurement module of the flow rate sensor.

the backup line of the NO delivery device connects fluidly to the injection line by an upstream end, upstream of the valve device, and by a downstream end, downstream of the valve device, so as to bypass said valve device.

the NO delivery device comprises a backup NO dosing system comprising the backup line.

the flow rate measurement device of the NO delivery device is arranged on the injection line, upstream or downstream of the valve device, preferably downstream of the valve device.

the NO conveying line of the NO delivery device conveys a gas mixture formed of NO and nitrogen, preferably an NO/N2 gas mixture containing between 100 and 2,000 ppmv of NO, typically less than 1,000 ppmv of NO, the remainder being nitrogen (and possibly unavoidable impurities).

the backup solenoid valve of the NO delivery device is configured and/or operated so that it is normally open.

the backup solenoid valve of the NO delivery device is an all-or-nothing solenoid valve.

the control means of the NO delivery device comprise at least one microprocessor.

the control means of the NO delivery device comprise a circuit board bearing said at least one microprocessor.

the injection line of the NO delivery device is fluidly connected to a high-pressure line by way of a pressure-regulating device, the high-pressure line and the pressure-regulating device being arranged in the NO delivery device.

the NO delivery device comprises a casing.

the backup NO dosing system is arranged in the casing of the NO delivery device, in particular the backup line and the backup solenoid valve.

the valve device of the NO delivery device comprises a solenoid valve, preferably a proportional solenoid valve.

the flow rate control device of the NO delivery device is configured to form, constitute or comprise a proportional calibrated orifice, that is, to form a proportional calibrated orifice system.

the flow rate control device comprises a proportional calibrated orifice system commanded by the control means in order to regulate the pre-set backup gas flow rate.

the control means of the NO delivery device are further configured to, prior to any interruption of the reception or loss of the signal(s) coming from the flow rate sensor, act on the proportional calibrated orifice system of the flow rate control device of the backup line to pre-regulate (i.e. regulate or adjust before any loss of signal) the desired backup gas flow rate, i.e. backup NO/N2 flow rate, which is determined on the basis of the respiratory gas flow rate having been measured by the flow rate sensor, before the interruption of reception of said signal, i.e. loss of signal, and on the basis of the desired NO dosage.

the flow rate control device of the NO delivery device comprises an actuator means interacting with a movable element comprising a through-slot, said movable element being able to be angularly displaced by the actuator means.

the actuator means comprises an electric motor driving a rotary shaft, the movable element being rigidly connected to said rotary shaft.

the electric motor is a stepping motor.

the movable element is arranged movably in an inner housing comprising an inlet port and an outlet port in fluid communication with the backup line.

the movable element is a sphere, that is, spherical, for example a ball or similar.

the inner housing has a spherical shape that complements the shape of the spherical movable element.

the control means are configured to operate the actuator means in order to perform an angular displacement of the movable element between at least:

a fully open position corresponding to a fully open level of the calibrated orifice of the flow rate control device, a fully closed position corresponding to a fully closed level (i.e. shut-off) of the calibrated orifice of the flow rate control device, and at least one intermediate position situated between said fully open position and said fully closed position, corresponding to a partially open level of the calibrated orifice of the flow rate control device.

the control means of the NO delivery device are configured to operate the actuator means in order to perform an angular displacement of the movable element between at least:

a fully open position in which the entire gas flow conveyed by the backup line enters the through-slot of the movable element, that is, a maximum flow rate, a fully closed position in which no gas flow can pass through the through-slot of the movable element, that is, a zero flow rate, and at least one intermediate position situated between said fully open position and said fully closed position, in which only part of the gas flow conveyed by the backup line enters the through-slot of the movable element, that is, one or more reduced flow rates.

the control means of the NO delivery device are configured to operate the actuator means in order to perform an angular displacement of the movable element between a plurality of intermediate positions angularly offset from each other, each corresponding to a level of opening of the calibrated orifice and/or to a given gas flow rate, that is, reduced flow rates between the maximum flow rate and the zero flow rate.

the control means of the NO delivery device are configured to operate the actuator means to regulate or adjust the backup gas flow rate, before any loss of signal coming from the flow rate sensor.

the control means of the NO delivery device are configured to determine a given calibrated orifice opening corresponding to the backup flow rate.

the control means of the NO delivery device are configured to determine the given calibrated orifice opening and/or the backup flow rate on the basis of a lookup table.

the NO delivery device comprises electrical power supply means supplying electrical current to the components requiring electricity to operate, in particular the control means.

the electrical power supply means comprise means for connection to the mains (110/220V) and/or a battery or similar.

the backup gas flow rate is determined by the control means on the basis of the last flow rate measurement(s) of the respiratory gas flow (i.e. air or N2/O2) circulating in the inhalation branch, having been taken by the flow rate sensor, before the malfunction (i.e. loss of signal), and transmitted to the control means of the NO delivery device. The control means further use the desired NO dosage in the final gas mixture, typically between 1 and 80 ppmv, to determine the backup gas flow rate.

In addition, the installation for supplying gas to a patient further comprises:

at least one source of NO containing an NO/N2 gas mixture and supplying said NO/N2 gas mixture to the NO delivery device.

a patient circuit comprising an inhalation branch supplied with the NO/N2 gas mixture by the NO delivery device, and with a respiratory gas containing oxygen, typically approximately at least 21% oxygen, such as air or an O2/N2 mixture, by the medical ventilator, i.e. a respiratory assistance apparatus.

the medical ventilator delivers air or an oxygen/nitrogen mixture (i.e. O2/N2).

the medical ventilator comprises a motorized blower (i.e. also referred to as a turbine, compressor or similar) delivering the respiratory gas, typically air or an oxygen/nitrogen mixture.

- the medical ventilator comprises a motorized blower controlled by control means, such as an electronic control board, arranged in the shell of the medical ventilator.
- the medical ventilator is an HFO (High Frequency Oscillation) ventilator or a conventional ventilator, such as a critical care ventilator.
- the NO source contains an NO/N2 gas mixture containing between 100 and 2,000 ppmv of NO, the remainder being nitrogen (N2), stored at a pressure of between 10 and 250 bar absolute, typically at more than 100 bar absolute (before the start of withdrawal).
- the NO source contains an NO/N2 gas mixture containing between 100 and 1,000 ppmv of NO, the remainder being nitrogen (N2), stored at a pressure of between 10 and 250 bar absolute, typically at more than 100 bar absolute (before the start of withdrawal).
- the NO source is one or more pressurized gas cylinders.
- the NO source is one or more gas cylinders having a capacity of between 0.5 and 50 l (water equivalent).
- the gas cylinder comprises a cylindrical body made from steel or an aluminium alloy.
- the gas cylinder is provided with a simple valve (without regulator) or a valve with an integrated regulator or IPR.
- the gas cylinder is provided with an IPR protected by a protective cap, for example made from metal or a polymer.
- the patient circuit comprises an inhalation branch and an exhalation branch.
- the patient circuit comprises flexible ducts forming the inhalation branch and/or the exhalation branch, typically polymer hoses.
- the inhalation branch and the exhalation branch, e.g. flexible ducts, are connected to a joining piece, such as a Y-piece.
- the inhalation branch and/or the exhalation branch is/are fluidly connected to a patient respiratory interface, preferably via the joining piece.
- the patient respiratory interface comprises a tracheal intubation tube or a breathing mask.
- the inhalation branch and the exhalation branch comprise flexible ducts, for example made from a polymer.
- the inhalation branch and the exhalation branch are further respectively fluidly connected to outlet and inlet orifices of the medical ventilator.
- the inhalation branch of the patient circuit can comprise a gas humidifier.
- the gas humidifier is arranged downstream of the NO injection module in such a way as to be able to humidify the gas before it is administered by inhalation to the patient.
- the concentration or dosage of NO in the final gas mixture, that is, the gas inhaled by the patient, after the NO/N2 mixture has been mixed with the respiratory gas containing at least 21% by volume of oxygen coming from the ventilator, such as air or an O2/N2 mixture, is between 1 and 80 ppm by volume (ppmv), depending on the population treated, i.e. newborns or adults, the condition of the patient and/or the disease to be treated.

The invention also relates to the use of a gas supply installation and/or of the NO delivery device according to the invention, provided with the backup NO dosing system of the invention, which are particularly suitable for use in a therapeutic treatment method including the supply of a gas mixture comprising 1 to 80 ppmv of NO (dosage) and approximately at least 21% by volume of oxygen and generally nitrogen to a patient (i.e. an adult, a child, an adolescent or a newborn) in need thereof, which patient is suffering from pulmonary hypertension and/or hypoxia, which can cause pulmonary vasoconstriction or similar, typically resulting from or caused by pulmonary diseases or disorders such as PPHN (persistent pulmonary hypertension of the newborn) or ARDS (acute respiratory distress syndrome), or resulting from or caused by heart surgery with placement of the patient on extracorporeal circulation (ECC).

BRIEF DESCRIPTION OF THE VIEWS OF THE DRAWINGS

The invention will now be better understood from the following detailed description, which is given by way of non-limiting illustration, with reference to the appended figures, in which.

DETAILED DESCRIPTION

Figure 1:
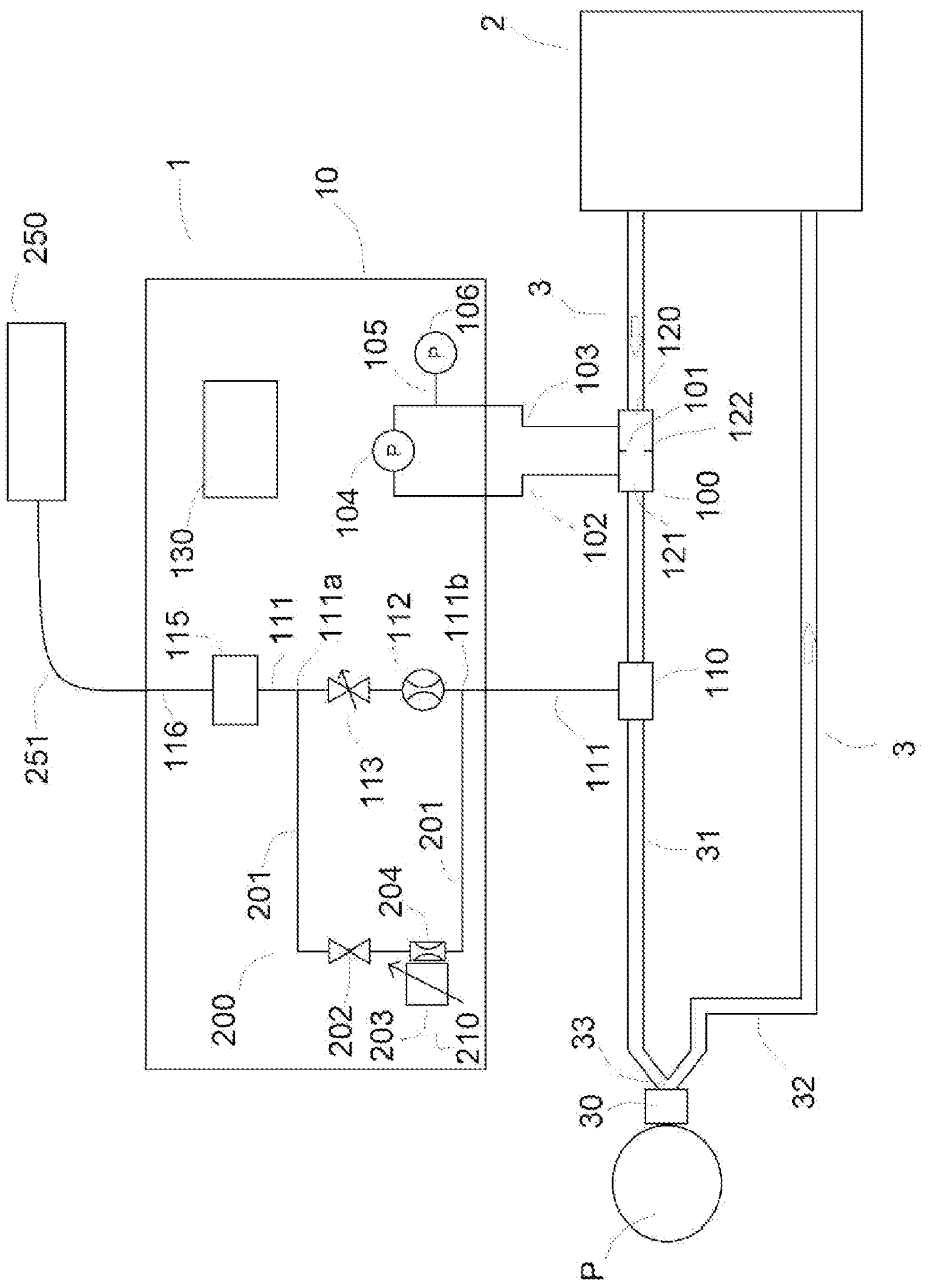
FIG. 1 is a schematic representation of a gas delivery installation provided with an emergency NO dosing system according to the present invention.

FIG. 1 is a schematic representation of an embodiment of a gas delivery installation 1, 2 according to the present invention, comprising an NO delivery device 1, comprising an emergency NO dosing mechanism, associated with a mechanical ventilator 2, that is a respiratory assistance apparatus delivering a respiratory gas, making it possible to deliver NO in gaseous form to a patient at a desired concentration corresponding to a dosage set by an anesthetist or similar, typically between 1 and 80 ppmv of NO (i.e. ppm by volume).

The medical ventilator 2 delivers a respiratory gas containing at least 21% oxygen, such as air or an NO/N2 mixture, into a patient circuit 3, in particular into an inhalation branch 31 of said patient circuit 3, serving to convey and supply the respiratory gas to a patient P during their inhalation phases, that is, to supply respiratory assistance to the patient P, and to transport the gases exhaled by the patient during their exhalation phases.

The medical ventilator 2 is a conventional apparatus comprising for example a motorized blower, also known as a turbine or compressor, delivering the respiratory gas into the patient circuit 3 and the operation of which is controlled by one or more electronic control board(s) or similar. It is supplied with electricity by electrical power supply means, such as the mains (110/22V) and/or an internal battery.

As can be seen in FIG. 1, the patient circuit 3 here comprises an inhalation branch 31 and an exhalation branch 32 fluidly connected to a Y-piece 33 or similar, in fluid communication with a respiratory interface 30 for delivering the gas to the patient P or for collecting the gases exhaled by said patient P. The respiratory interface 30 can for example be a face mask or an intubation tube.

The inhalation branch 31 and exhalation branch 32 comprise ducts, channels, hoses, passages, tubes or similar, for example flexible polymer hoses that are able and configured to transport the gas flows.

The respiratory gas circulating in the inhalation branch 31 of the patient circuit 3, that is, going from the mechanical ventilator 2 to the patient P, is inhaled by the patient P, whilst the gases exhaled by said patient P, i.e. gases rich in CO2, follow the exhalation branch 32 of the patient circuit 3 towards the mechanical ventilator 2 in order to be released to the atmosphere by the mechanical ventilator 2.

Moreover, a flow rate sensor 100 and an NO injection module 110 are positioned in the inhalation branch 31 of the patient circuit 3. The flow rate sensor 100 is preferably positioned in the inhalation branch 31 between the NO injection module 110 and the mechanical ventilator 2.

The inhalation branch 31 can also comprise a humidifier (not shown) in order to humidify the gas delivered to the patient P. Preferably, the humidifier is placed downstream of the NO injection module 110, that is, between said NO injection module 110 and the respiratory interface 30 supplying the gas to the patient P.

The flow rate sensor 100 is used to measure the gas flow, i.e. a flow rate, delivered by the mechanical ventilator 2 and circulating in the inhalation branch 31. The flow rate sensor 100 can be a sensor that measures and supplies flow rate signals or measurements per se, for example a mass flow sensor, or that measures and supplies pressure signals or measurements that are then converted into a flow rate by the control means, for example a differential pressure measurement sensor, also known as a differential pressure sensor.

In the embodiment in FIG. 1, the flow rate sensor 100 is of the type that measures differential pressure, that is, the flow rate sensor 100 comprises a measurement module 100-1 comprising an internal restriction 101 that creates a pressure drop generating a pressure differential or gradient when a gas flow passes through the internal restriction 101.

As can be seen in FIG. 1, the measurement module 100-1 of the flow rate sensor 100 comprises upstream 120 and downstream 121 chambers that are separated by a wall 122 through which a gas passage extends so as to form the internal restriction 101. An upstream line 103 and a downstream line 102 for pressure measurement, i.e. pneumatic lines, such as gas ducts, are fluidly connected to the measurement module 100-1 of the flow rate sensor 100 at connection sites situated upstream and downstream of the internal restriction 101, in particular to the upstream 120 and downstream 121 chambers, in order to take the pressure measurements of the circulating flow, before and after the pressure drop.

The pressure difference created by the internal restriction 101 is determined by a differential pressure sensor 104 connected to the flow rate sensor 100 by way of the upstream 102 and downstream 103 lines, which form pressure measurement ducts and supply the differential pressure sensor 104 with the pressure measurements of the circulating flow, before and after the pressure drop. Preferably, the differential pressure sensor 104 is integrated into the casing 10 of the NO delivery device 1. The sensor 104 can either be connected electrically to an operating unit 130, also known as control means 130, or can transmit the pressure measurements thereto so that they are processed by computer.

The operating unit 130, i.e. the control means 130, comprises a system for processing data, i.e. measurements, comprising for example one or more microprocessors arranged on one or more electronic boards and implementing one or more algorithms, i.e. one or more computer programs.

In other words, the operating unit 130 is configured to process and/or exploit the pressure measurement signals or the pressure values transmitted by the differential pressure sensor 104 interacting with the flow rate sensor 100.

For example, the operating unit 130 has a pre-recorded lookup table that makes it possible to determine the flow rate of gas circulating in the inhalation branch 31 and the measurement module 100-1 of the flow rate sensor 100, that is, makes it possible to convert a pressure value transmitted by the differential pressure sensor 104 into a value of the flow rate passing through the measurement module 100-1 of the flow rate sensor 100.

Such determining of the flow rate passing through the flow rate sensor 100 then makes it possible to calculate the quantity of NO that must be added to the gas circulating in the inhalation branch 31 before it reaches the patient P.

In other words, using the pressure measurement returned by the differential pressure sensor 104 and the lookup table, the operating unit 130 can determine the gas flow rate issuing from the mechanical ventilator 2 and the quantity of NO that must be added, via the NO injection module 110, in order to obtain the desired concentration of NO, i.e. the dosage defined by the physician, that must be inhaled by the patient P.

Of course, the operating unit 130 can also be configured to operate other electromechanical elements integrated into the casing 10 or outer shell of the NO delivery device 1.

According to another embodiment (not shown), the flow rate sensor 100 could also be a mass flow sensor or similar connected directly to the control means 130, via one or more electrical connections, such as one or more cables or similar, in order to supply them with a signal, such as a voltage, or a measurement of the flow rate passing through the sensor 100. In this case, the differential pressure sensor 104 is removed.

In general, the final gas mixture, i.e. the NO-based respiratory gas that is then administered to the patient by inhalation, obtained in the NO injection module 110 arranged on the inhalation branch 31, then mainly comprises nitrogen (N2), oxygen (O2), typically at a content of approximately at least 21% by volume, and NO, at a content typically between 1 and 80 ppmv, for example of the order of 10 to 20 ppmv.

More specifically, during normal operation, depending on the gas flow rate (i.e. air or N2/O2) circulating in the inhalation branch 31 that has been determined by means of the flow rate sensor 100, the operating unit 130 determines the quantity of NO, typically a mixture of NO and N2, that must be added to the gas circulating in the inhalation branch 31 by the NO injection module 110 in order to obtain the concentration or dosage desired, that is, set by the physician or similar, during normal operation of the gas supply installation 1, 2.

Typically, the concentration or dosage of NO in the gas inhaled by the patient, after the NO/N2 mixture has been mixed with the air or an O2/N2 mixture, is between 1 and 80 ppm by volume (ppmv), for example of the order of 10 to 20 ppmv, depending on the population treated, i.e. newborns or adults, and therefore the disease to be treated.

The NO delivery device 1 is supplied with gaseous NO, typically in an NO/N2 gas mixture, coming from an NO source 250 fluidly connected to the NO delivery device 1, in particular to a high-pressure line 116 of said NO delivery device 1, via a supply line 251, such as a flexible duct or similar.

Typically, the NO source 250 is one or more pressurized gas cylinders holding an NO/N2 mixture containing an NO concentration generally between 100 and 2,000 ppmv, preferably between 200 and 1,000 ppmv, for example of the order of 800 ppmv, and stored at a pressure (when completely full) that can be up to 200 to 250 bar absolute, or even more.

The NO/N2 mixture is supplied to the injection module 110 by the NO delivery device 1 via an injection line 111, such as a flexible gas duct.

The injection line 111 situated in the casing 10 of the NO delivery device 1 is fluidly connected to a high-pressure line 116 of the NO delivery device 1, which high-pressure line 116 has a high-pressure inlet fluidly connected to the NO source in order to be supplied with pressurized NO/N2, that is, at a pressure that can be up to 200 bar absolute.

The high-pressure line 116, for example a gas passage or duct, is also arranged in the casing 10 of the NO delivery device 1 and comprises a pressure regulator 115 that reduces the pressure of the NO/N2 mixture to a stable value, for example 4 bar absolute. The outlet port of the pressure regulator 115 supplies a stable pressure in the upstream portion of the injection line 111.

A valve device 113, such as a solenoid valve, preferably a proportional solenoid valve, such as the Parker miniature VSO series for example, is arranged in the device 1 in order to control the flow rate of gaseous NO within the injection line 111. The flow rate of gas circulating in the injection line 111 is measured by a flow rate measurement device 112, also known as an NO flow rate sensor, arranged on the injection line 111, preferably placed downstream of the solenoid valve 113, as can be seen in FIG. 1.

The pressure regulator 115, the valve device or solenoid valve 113, the NO flow rate sensor 112 and a portion of the injection line 111 are thus arranged in the casing 10 of the NO delivery device 1.

The valve device 113 is configured so that it is normally in a closed position (i.e. an idle state) in order to prevent any circulation of gas in the injection line 111.

Advantageously, in the idle state, the valve device 113 is not operated by the control means. In other words, when the control means 130 stop/cease commanding the valve device 113, it automatically switches/returns to the idle state, that is, a closed position.

Conversely, in order to switch to an open position, the valve device 113 must be commanded by the control means 130, as is the case during normal operation of the gas supply installation 1, 2.

Moreover, according to the invention a backup NO dosing system 200 is provided, arranged in the casing 10 of the NO delivery device 1 and used in the event of a failure, as set out in detail below.

The backup NO dosing system 200 comprises a backup line 201, also called a bypass line, such as a gas passage, a gas duct or similar. The backup line 201 fluidly connects to the injection line 111 at a first connection site 111*a* situated upstream of the valve device 113, such as a proportional solenoid valve, and here downstream of the pressure regulator 115, and at a second connection site 111*b* situated downstream of the valve device 113, and preferably downstream of the NO flow rate sensor 112.

In other words, a valve device 113, such as a proportional solenoid valve, and preferably the NO flow rate sensor 112, are situated between the first and second connection sites 111*a*, 111*b* of the emergency line 201, that is the emergency line 201 bypasses the valve device 113 and preferably the NO flow rate sensor 112 situated on the injection line 111. According to another embodiment, the second connection site 111*b* can be situated downstream of the valve device 113 and upstream of the NO flow rate sensor 112, that is, between these two elements.

The backup line 201 comprises, for its part, a backup solenoid valve 202 and a flow rate control device 210 forming part of the backup dosing system 200 of the invention. This backup solenoid valve 202 is configured so that it is normally in an open position (i.e. an open state) in order to allow gas to circulate in the backup line 201.

The flow rate control device 210 in fact forms a proportional calibrated orifice system 204 that makes it possible to adjust or regulate the backup flow rate of gas, i.e. NO/N2 mixture, circulating in the backup line 201. It can take various forms, i.e. arrangements, in particular the arrangement illustrated in FIG. 2 to FIG. 5 and set out in detail below.

The backup solenoid valve 202 is preferably an "all-or-nothing" solenoid valve having two possible states, namely an open state and a closed state, for example an IMI Norgren Picosol series solenoid valve.

The backup solenoid valve 202 is normally open, that is, in the absence of an electrical command from the operating unit 130, the backup solenoid valve 202 is in its idle state, i.e. in an open position, which then allows the gas coming from the NO source to follow the backup line 201 from the first connection site 111*a* towards the second connection site 111*b*.

In other words, as above for the valve device 113, in its idle state, the backup solenoid valve 202 is not operated by the control means 130. In other words, when the control means 130 stop/cease commanding the backup solenoid valve 202, it automatically switches/returns to the open position that corresponds to its idle state.

Again, it is the control means or operating unit 130 that ensure that the backup solenoid 202 closes, that is, that it switches from the idle state (i.e. open position) to its active state, that is a closed position, as is the case during normal operation of the gas supply installation 1, 2.

In other words, the control means 130, i.e. the operating unit, are configured to interact with the backup solenoid valve 202, the flow rate control device 210, the valve device 113 and the flow rate measurement device 112, during normal operation of the device 1 and the gas supply installation 1, 2.

In the embodiment shown in FIG. 2 to FIG. 5, the flow rate control device 210 comprising or forming a proportional calibrated orifice system, that is, constituting, including or forming a proportional calibrated orifice 204, comprises an actuator means 203 interacting with a movable element 2042 arranged in a compartment 2041, said movable element 2042 comprising a through-slot 2043.

However, the flow rate control device 210 constituting the proportional calibrated orifice 204 can take another form, for example a needle valve device or an assembly comprising a pressure regulator arranged upstream of a fixed orifice, said pressure regulator being able to be set to different output pressures, thus generating different flow rates through said fixed orifice.

Figure 2:
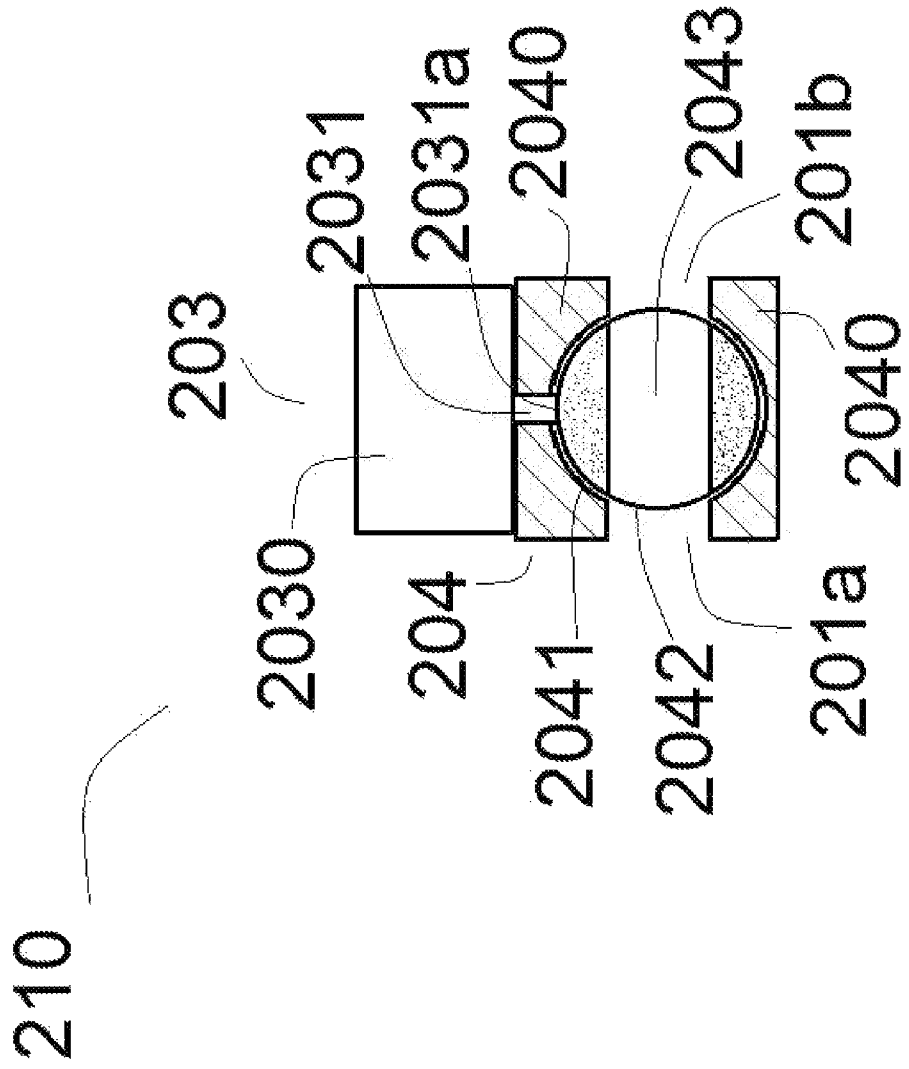
FIG. 2 is a schematic representation of the association between the calibrated orifice and the actuator in the emergency NO dosing system in FIG. 1.

FIG. 2 thus shows a schematic cross-section of an embodiment of the flow rate control device 210, i.e. of the calibrated orifice 204, which is here formed by the actuator means 203 and the movable element 2041 associated with the through-slot 2043, of the emergency NO dosing system with which the NO delivery device 1 of the invention is provided.

The actuator means 203, more simply known as an actuator, in FIG. 2 is preferably a stepping motor 2030, for example as sold by Portescap, extended by a shaft 2031 mechanically coupled at 2031*a* to the movable element 2042.

Moreover, here, the movable element 2042 is a sphere. The sphere forming the movable element 2042 can be made from metal, for example stainless steel, and has a through-slot 2043, that is, it is diametrically traversed by an internal hole or passage allowing the passage of the gas. The movable element 2042, i.e. the sphere, is housed in an internal compartment or housing 2041 forming a sphere chamber, which here is generally spherical. The housing 2041 is formed in a part forming a body 2040. The outer diameter of the sphere 2042 is substantially equal to the inner diameter of the internal housing 2041.

The part forming a body 2040 can also be made from metal, for example a steel ball or similar. It comprises an inlet port 201*a* and an outlet port 201*b* in fluid communication with the internal housing 2041.

FIG. 2 shows that the through-slot 2043 of the sphere 2042 is aligned with the inlet port 201*a* and outlet port 201*b* of the body 2040, which are in fluid communication with the backup line 201, that is, they are fluidly continuous, so that the gas can to flow from the inlet port 201*a* to the outlet port 201*b* via the through-slot 2043 of the sphere 2042.

As indicated, here, the actuator means 203 is a stepping motor 2030 rotating the shaft 2031 and thus the sphere 2042. In response to a command coming from the operating unit 130, the stepping motor 2030 will adopt a different position and cause the rotation of the shaft 2031, which will then also rotate the sphere 2042.

Considering that the operating unit 130 is able to vary the command value proportionally, it follows that the shaft 2031 can undergo greater or lesser rotational movements in a proportional manner, for example between 0 and 90°. In other words, the rotational movement undergone by the shaft 2031 is therefore transmitted to the sphere 2042, which pivots in response, within its housing 2041, as illustrated in FIG. 3 to FIG. 5, which makes it possible to regulate or adjust the desired gas flow rate, during the normal operation of the apparatus 1.

Figure 3:
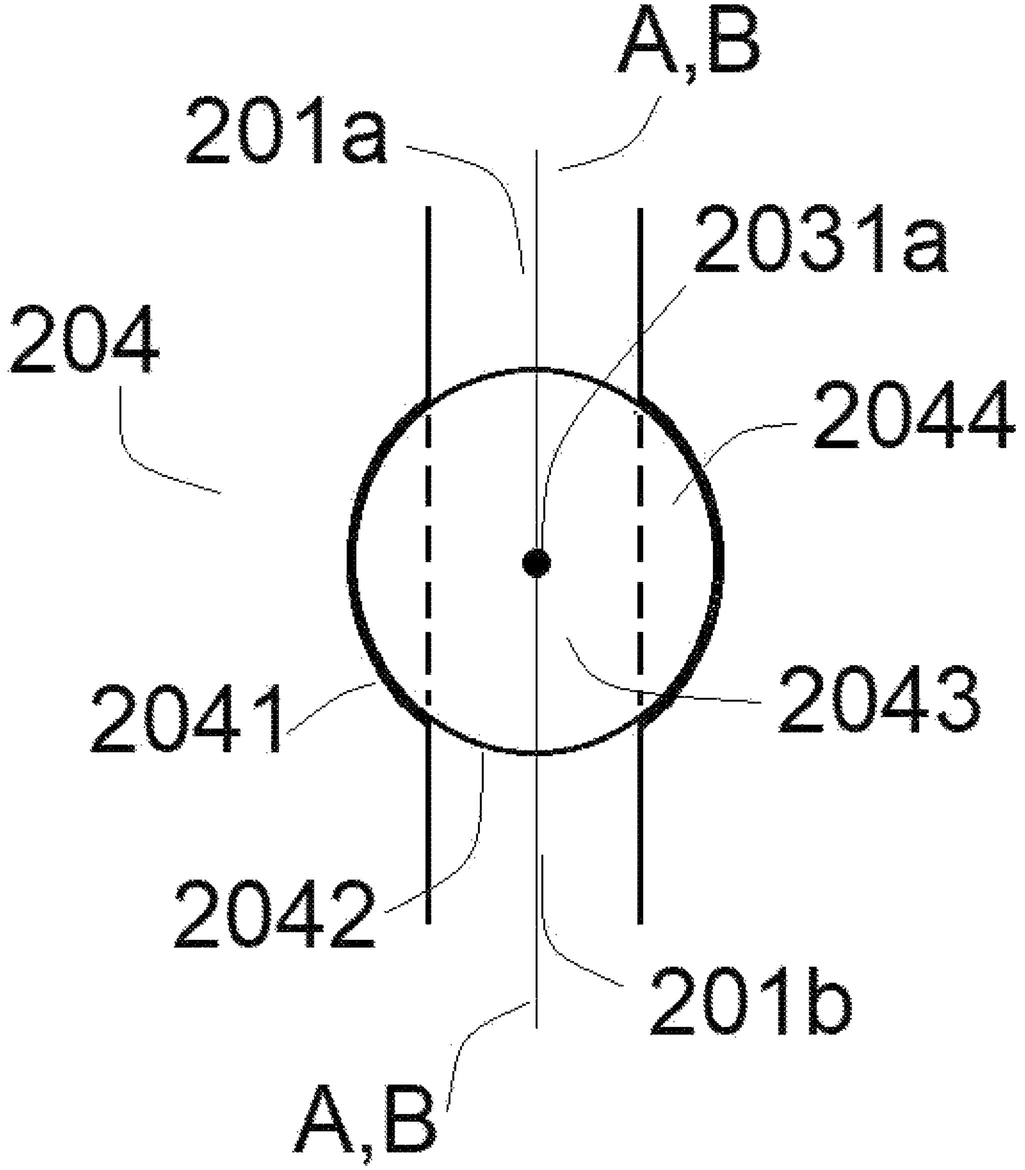
FIG. 3 to FIG. 5 are schematic representations of the operation of the association between the calibrated orifice and the actuator in FIG. 2.

FIG. 3 is thus a schematic top view of the calibrated orifice 204 in FIG. 2 and shows, as already explained, the shaft 2031 causing the sphere 2042 to present its slot 2043 continuously between the inlet port 201*a* and outlet port 201*b* of the body 2040, so as to create a fluid connection between said inlet and outlet ports 201*a*, 201*b* and thus permit the gas to pass through the ports 201*a*, 201*b* and the slot 2043. The calibrated orifice 204 is then at its maximum opening, that is, in a fully open position. In this position, the axis AA of the through-slot 2043 of the sphere 2042 is (quasi) coaxial with the axis BB passing through the inlet port 201*a* and outlet port 201*b*, so that the opening is at its maximum, hence maximum flow in the backup line 201, including through the through-slot 2043 of the sphere 2042.

Figure 4:
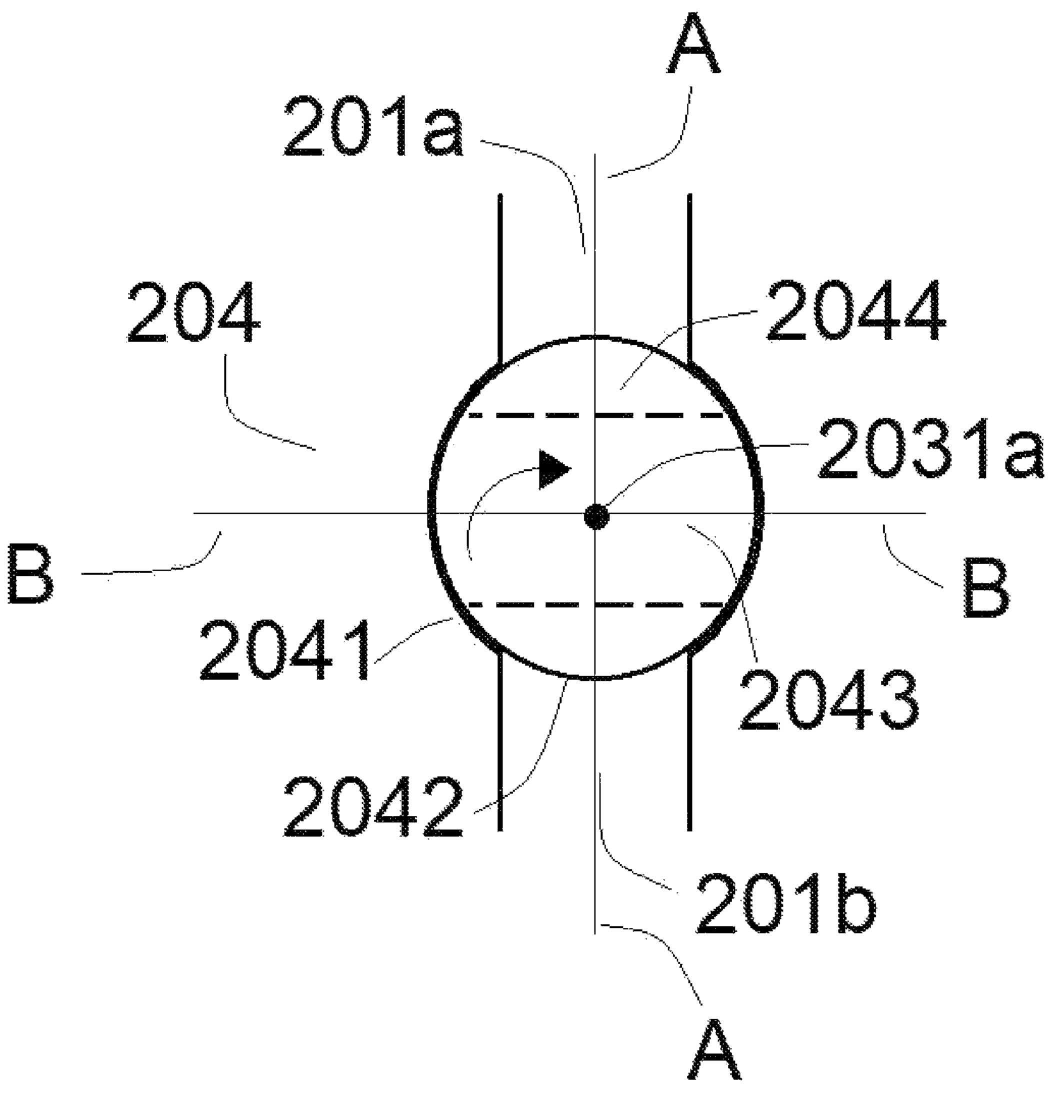
Figure 5:
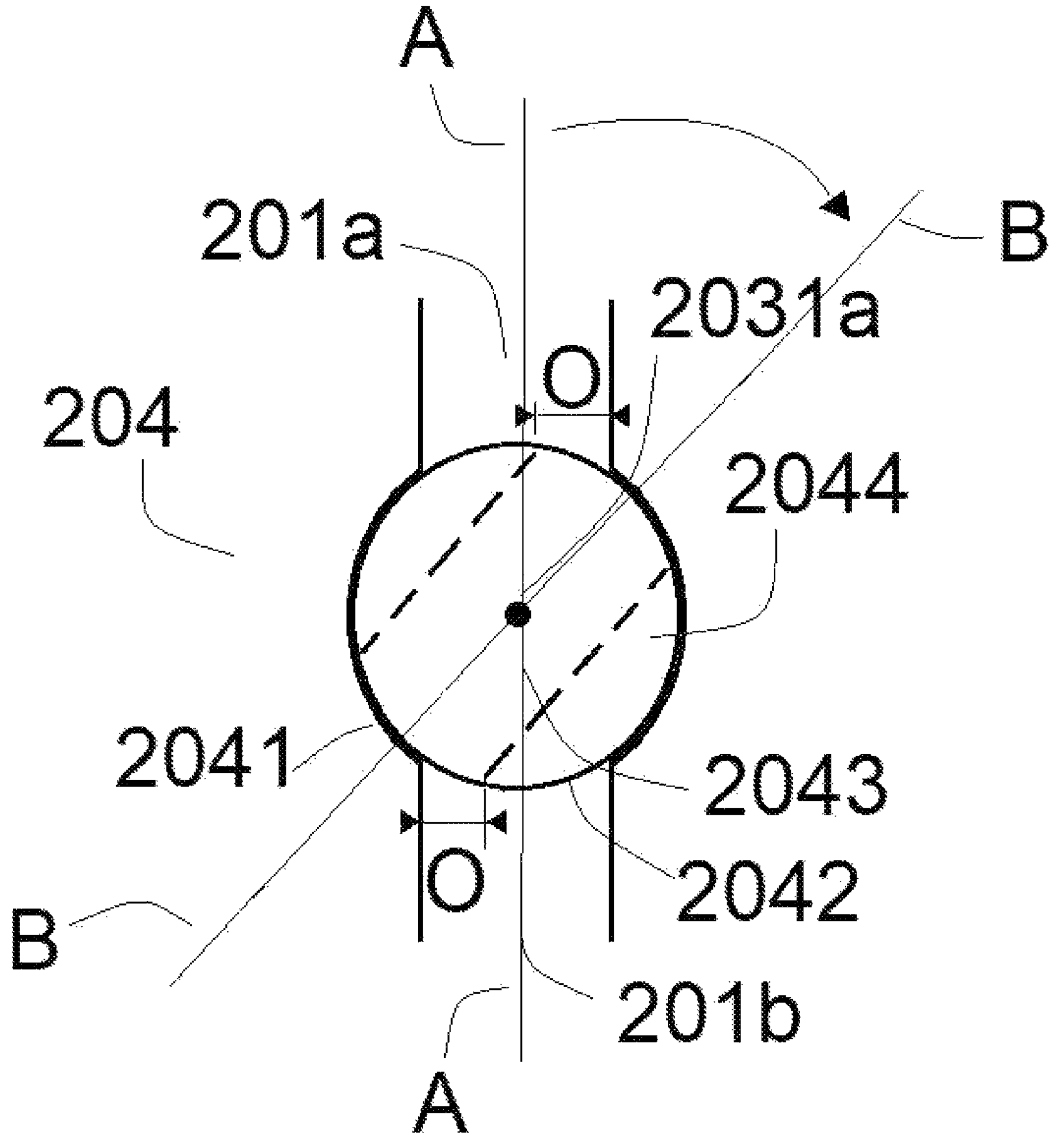

In FIG. 4, the operating unit 130 has commanded the stepping motor 2030 to cause the rotation of the shaft 2031, here of the order of 90°, and therefore also of the sphere 2042, which also undergoes the same 900 rotation. After rotation, the inlet port 201*a* and outlet port 201*b* of the body 2040 of the calibrated orifice 204 no longer face the slot 2043 of the sphere 2042 but instead face a non-hollow, i.e. solid, portion 2044 of the sphere 2042 and are thus completely shut off by the non-hollow part 2044 of the sphere 2042. The fluid connection is thus interrupted and no gas can circulate between the inlet port 201*a* and outlet port 201*b* of the body 2040 of the calibrated orifice 204. The calibrated orifice 204 is then fully closed.

In this so-called closed position, the axis AA of the through-slot 2043 of the sphere 2042 is (quasi) perpendicular to the axis BB passing through the inlet port 201*a* and outlet port 201*b*, so that no passage of gas takes place through the through-slot 2043 and therefore in the backup line 201.

Between FIG. 3 and FIG. 4, the operating unit 130 has imposed on the actuator 203 extreme command values, i.e. between 0° and 90° rotation, making it possible to obtain either complete communication (cf. FIG. 3) or complete isolation (cf. FIG. 4) of the inlet port 201*a* and outlet port 201*b* of the body 2040 of the calibrated orifice 204.

However, the operating unit 130 is also configured to be able to issue, in a proportional manner, commands causing the rotation of the shaft 2031 and of the sphere 2042 between these two extreme angular positions, i.e. 0° and 90° rotation, that is, an angle that is not zero but is less than 90°.

FIG. 5 thus gives the example of an intermediate angular position in which the sphere 2042 has undergone a rotational movement of the order of 45°. In this case, the inlet port 201*a* of the body 2040 of the calibrated orifice 204 is partially obstructed, that is, exposed to non-hollow 2044 and hollow 2043 parts of the sphere 2042. The gas flow area of the hollow part 2043 of the sphere 2042 in fluid communication with the inlet port 201*a* is then defined by a level (or size) of opening O. This gas flow area is always less than the maximum fluid connection area as shown in FIG. 3. By way of the axial rotation, the same level of opening O appears between the outlet port 201*b* and the hollow part 2043 of the sphere 2042 of the body 2040 of the calibrated orifice 204.

In the so-called intermediate positions, the axis AA of the through-slot 2043 of the sphere 2042 and the axis BB passing through the inlet port 210*a* and outlet port 201*b* form between them a variable angle, here strictly between 0 and 90°, so that the passage of gas through the through-slot 2043, therefore in the backup line 201, is limited/reduced but not zero, nor the maximum, that is, depending on the desired opening O of the calibrated orifice 204.

Depending on the command imposed on the actuator 203 by the operating unit 130, the level of opening O defined by the intersection of the inlet port 201*a*, the outlet port 201*b* and the hollow part 2043 of the sphere 2042 thus varies from a zero value (FIG. 3) to a maximum value (FIG. 4), that is, it can assume the intermediate values situated between these two extreme values, i.e. between 0 and 90°, which makes it possible to regulate or adjust the flow rate of gas circulating in the backup line 201.

It will be readily appreciated that each level or value of opening O corresponds to an equivalent calibrated orifice the gas flow area of which depends on the positioning of the sphere 2042 and consequently on the command sent by the operating unit 130, i.e. the control means, to the actuator 203.

As has already been stated, this assembly therefore forms a proportional calibrated orifice, since its diameter or level of opening O depends on the angular position adopted by the sphere 2042 within the body 2040 of the calibrated orifice 204.

The pressure prevailing in the upstream portion of the backup line 201, that is, upstream of the calibrated orifice 204, is stable and known, since it corresponds to the relief pressure of the pressure regulator 115, set for example at 4 bar absolute. The flow rate of gas circulating in the downstream portion of the backup line 201, that is, downstream of the calibrated orifice 204, therefore depends on the level of opening O.

The operating unit 130 can thus have a lookup table linking a given command level to a level of opening and to a flow rate of gas passing through the calibrated orifice 201 towards the injection line 111 and accessing the second connection site 111*b*.

For reasons of simplification, the pressure level prevailing in the inhalation branch 31 of the patient circuit 3, and therefore in the NO injection module 110 and the injection line 111, is considered to be negligible with regard to the relief pressure of the pressure regulator 115 and therefore has no impact on the accuracy of the measurements of the flow rate circulating in the backup line 201 taken by the operating unit 130.

Of course, according to a particular embodiment, supplementary measuring means, such as an additional pressure measurement device arranged to measure pressure downstream of the calibrated orifice 204 of the backup line 201, can be implemented, i.e. used, for compensation purposes, without changing the object of the present invention in any way.

Finally, it must be noted that the choice of a stepping motor is particularly recommended since, in contrast to the solenoid valves 202, 113, which will adopt an idle position if the power is cut, namely an open position for the all-or-nothing solenoid valve 202 and a closed position for the proportional solenoid valve 113, the position of the stepping motor remains permanent and fixed according to the last command imposed. In other words, the calibrated orifice 204 has a fixed level of opening corresponding to the last command value received by the stepping motor, i.e. the last command originating from the control means 130.

Of course, the present invention is not limited to an actuator in the form of a stepping motor. Any other actuator that keeps its position if the electrical power supply fails and that can be coupled to a mechanical mechanism making it possible to define a calibrated orifice of variable size can be used, for example a linear motor or similar.

Moreover, the NO delivery device 1 is supplied with electricity by an electrical power supply, for example the mains (110/220V) or an internal battery, in order to permit the correct operation of the components thereof that require electrical current in order to function, in particular the actuator 203, such an electric stepping motor, the operating unit 130, the solenoid valves 202, 113, or other components.

In addition, the NO delivery device 1 also comprises storage means, such as a computer memory, for storing data, information or similar, for example one or more lookup tables, the gas flow rate measurements taken by the flow rate measurement device 112 or coming from the flow rate sensor 100 and/or processed by the control means 130, or other data.

According to the invention, in the event that the operation of the installation 1, 2 fails as a result of a loss of signal, i.e. the measurements, coming from the flow rate sensor 100, for example in the event of the disconnection of the upstream 103 and/or downstream 102 pressure measurement lines, which can be mechanically coupled, it must be possible to continue to treat the patient with inhaled NO despite the malfunction.

To this end, in the event that the control means (130) lose the signal(s) coming from the flow rate sensor 100, the backup solenoid valve 202 ceases to be commanded by the control means 130 as it is during normal operation of the installation 1, 2, so that it automatically switches to an open position, that is, its idle state, to allow the circulation of a backup gas flow (i.e. NO/N2 mixture) in the backup line 201 and, at the same time, the valve device 113 also ceases to be commanded by the control means 130, so that it switches to a closed position, that is, its idle state, in order to stop any circulation of gas (i.e. NO/N2 mixture) in the injection line 111, which makes it possible to supply the gas (i.e. NO/N2 mixture) at a backup gas flow rate, via the backup line 201 and the flow rate control device 210, even if the signal is lost.

In this case, the backup gas flow rate corresponds to a gas flow rate pre-regulated in the flow rate control device 210 forming a proportional calibrated orifice system, during the normal operation of the installation, that is, before the loss of signal from the flow rate sensor 100.

More specifically, the backup gas flow rate corresponds to the "last" flow rate calculated by the control means 130 on the basis of the last measurement signal(s) corresponding to the flow rate(s) of respiratory gas (e.g. air or N2/O2) in the inhalation branch, having been supplied by the flow rate sensor 100 of the patient circuit 3 to the control means 130, before said interruption of reception of said signal, and also on the basis of the desired NO dosage, which is typically between 1 and 80 ppmv. The desired NO dosage or concentration in the final mixture is set by the medical staff, e.g. a physician or similar, and can be stored in the NO delivery device 1.

Preferably, the backup gas flow is calculated on the basis of a plurality of flow rate values measured by the flow rate sensor 100 within the inhalation branch of the patient circuit 3, during normal operation of the installation 1, 2. Said flow rate values are averaged by the control means, that is, the control means 130 calculate an average gas flow rate or "average flow rate" over a given period of time, during which the values were read, for example for several seconds or tens of seconds. The backup gas flow rate is then pre-regulated in the flow rate control device 210 forming the proportional calibrated orifice system, also during normal operation of the installation 1, 2.

In other words, during normal operation of the installation 1, 2 prior to the malfunction, the backup gas flow rate is determined by the control means 130 on the basis of the last gas flow rate measurement(s) supplied by the flow rate sensor 100, in particular an average flow rate, as explained above, and optionally stored, and of course on the basis of the desired dosage, i.e. the NO content in the final mixture. The control means 130 can then act immediately, that is before any future loss of signal, on the flow rate control device 210 of the NO supply device 1 in order to adjust the calibrated orifice thereof so that it is able to immediately deliver a backup gas flow (i.e. NO/N2 mixture) at the desired backup gas flow rate via the backup line 201, as soon as a loss of signal is detected and the control means 130 cease or stop commanding the backup solenoid valve 202 and the valve device 113, which then switch to their respective idle states, namely to an open position for the backup solenoid valve 202 and to a closed position for the valve device 113 so as to ensure the circulation of the NO/N2 gas mixture in the backup line 201 but prevent or stop any circulation of gas in the injection line 111.

The control means 130 therefore determine the backup gas flow rate, before any loss of signal, on the basis of the desired NO dosage and the last gas flow rate measurement(s) supplied by the flow rate measurement device 100, during normal operation, that is before any interruption of the signal, and act on the flow rate control device 210 in order to pre-regulate this backup gas flow rate, for example by adjusting the diameter or level of opening O acting on the angular position adopted by the sphere 2042 within the body 2040 of the calibrated orifice 204, as explained above. Preferably, the last flow rate measurements are used by the control means 130 to calculate an average flow rate over a given duration of a few seconds or tens of seconds preceding the malfunction and this average flow rate is used to determine the backup gas flow rate making it possible to obtain the desired dosage.

More specifically, the operation of the backup NO dosing system 200 of the NO delivery device 1 of the invention is generally as follows.

As illustrated in FIG. 1, the NO delivery device 1 interacts with a mechanical ventilator 2 in order to provide therapeutic aid to the patient P. As already explained, the flow rate of the flow of respiratory gas containing oxygen, typically approximately at least 21% by volume of O2 (e.g. air or N2/O2, or even pure O2) coming from the mechanical ventilator 2 and circulating in the inhalation branch 31 of the patient circuit 3 is continuously measured by the flow rate sensor 100 and transmitted to the operating unit 130, as set out above depending on whether the flow rate sensor 100 is a flow rate sensor per se or a differential pressure measurement sensor.

These flow rate measurements allow the operating unit 130 to determine, in real time, the flow rate of NO, i.e. the backup flow rate, that must be injected into the injection line 111 and the NO injection module 110 in order to satisfy the desired concentration or dosage of NO in the gas supplied to the patient, namely between 1 and 80 ppmv, typically between 5 and 80 ppmv, for example of the order of 10 to 20 ppmv.

In normal operation, the operating unit 130 commands the valve device 113, preferably a proportional solenoid valve, to an open position (i.e. active state) to allow the circulation of the NO/nitrogen mixture in the injection line 111. Conversely, so as not to introduce an additional flow coming from the backup line 201 into the injection line 111, the operating unit 130 commands the solenoid valve 202, which is preferably an all-or-nothing solenoid valve, to a closed position (i.e. active state) and, in parallel, will operate the actuator 203, i.e. the stepping motor, in order to pre-regulate the calibrated orifice 204 by defining a given level of opening O, and therefore a backup flow rate.

This is carried out as follows by the operating unit 130, on the basis of one or preferably a plurality of measurements of the flow rate of respiratory gas (e.g. air or N2/O2, or even O2) coming from the ventilator 2, which circulates in the inhalation branch 31 of the patient circuit 3 at a flow rate(s) determined by the flow rate sensor 100, which is transmitted to the control means 130.

The operating unit 130 uses the respiratory gas flow rate measurements to preferably calculate an average flow rate over a given duration, for example a few seconds, and then evaluate the NO flow rate value (in 1/min) that makes it possible to obtain or come close to the desired NO concentration or dosage, e.g. between 1 and 80 ppmv, for example of the order of 10 to 20 ppmv, after the flow of NO/nitrogen mixture conveyed by the injection line 111 has been mixed with the respiratory gas circulating in the inhalation branch 31 of the patient circuit 3. In other words, the calculation of the NO flow rate value takes into account, during normal operation of the installation, the respiratory gas flow rate measured in the patient circuit 3 by the flow rate sensor 100, in particular an average flow rate calculated by the control means 130.

More specifically, when the backup flow rate value has been determined, the operating unit 130 carries out a conversion by way of a stored lookup table so as to command the actuator 203 of the flow rate control device 210 and consequently define a level of opening of the calibrated orifice 204 in order to set a flow rate of NO that can circulate in the backup line 201 equal to the calculated average NO value set, that is, corresponding to the pre-set backup flow rate. It must be emphasized that this activity has no physical effect, i.e. no flow of gas circulates in the backup line 201, because the all-or-nothing solenoid valve 202 is closed during normal operation of the installation 1, 2, that is, before any loss of signal coming from the flow rate sensor 100.

Conversely, in the event that the signal coming from the flow rate sensor 100 is interrupted, the valve device 113, typically a proportional solenoid valve, returns to its idle state, namely switches to its closed position preventing any passage of gas, while the solenoid valve 202 simultaneously returns to its idle state, namely its open position, permitting the gas coming from the NO source to pass into the backup line 201 and circulate as far as the second connection site 111*b* and then the downstream part of the injection line 111. The operating unit 130 has ceased to operate the valve device 113 and the backup solenoid valve 202, which have automatically returned to their idle state.

In other words, the valve device 113, typically a proportional solenoid valve, and/or the solenoid valve 202 switch naturally to their idle state, that is, independently of any command from the control means 130. These idle states are in fact "default" states of the valve device 113 and the solenoid valve 202.

The NO/N2 mixture can then circulate in the backup line 201 at a backup flow rate calculated as explained above and set out below, which is controlled by the calibrated orifice of the flow rate control device 210. The flow of NO/N2 at the backup flow rate reaches the injection line 111 (at 111*b*) and can then be injected into the inhalation branch 31 of the patient circuit 3 via the NO injection module 110, as already explained, in order to obtain the final mixture to be administered to the patient, which is at the desired NO dosage, that is, usually between 1 and 80 ppmv of NO, for example of the order of 10 to 20 ppmv.

It will therefore be understood that, according to the invention, the flow rate control device 210 is configured, i.e. pre-regulated during normal operation of the installation 1, 2 to supply, in the event of a malfunction with loss of signal from the flow rate sensor 100, the gas, i.e. NO/N2, at a backup gas flow rate determined by the control means 130 on the basis of one or more gas flow rate measurement(s) supplied by the flow rate sensor 100, for example via the upstream and downstream lines 103, 102, and the differential pressure sensor 104 before any malfunction, preferably the last flow rate value of the respiratory gas coming from the ventilator 2 and measured before the malfunction, caused for example by the inadvertent or accidental disconnection of the upstream and downstream lines 103, 102, or even the abrupt failure of the flow rate sensor 100.

The NO flow rate value is therefore pre-regulated within the flow rate control device 210 by the control means 130, for example by acting on the angular position adopted by the sphere 2042 within the body 2040 of the calibrated orifice 204 of the flow rate control device 210 in order to vary the diameter or level of opening O therein, as explained above, by command of said flow rate control device 210 by the control means 130, said pre-regulation taking place, that is to say being performed or realised, during said normal operation of the device 1.

Of course, injecting a continuous flow rate of NO into the inhalation branch 31 of the patient circuit 3 does not guarantee the same accuracy of the inhaled NO concentration as when the NO delivery system 1 is operating normally, that is by adjusting the flow rate of NO according to the flow rate passing through the flow rate sensor 100, but the buffer volume generated by the portion of the inhalation branch 31 situated downstream of the NO injection module, which is optionally augmented by the volume of the humidification chamber when it is present, makes it possible to smooth the variations in the concentration of NO inhaled by the patient and to come close to the desired target value, that is to say the NO dosage.

In any event, being able to come close to the desired target value of NO, by virtue of the backup NO dosing system 200 integrated into the NO delivery device 1 of the invention, considerably improves the safety for the patient by comparison with a fixed backup NO flow rate (for example of 250 ml/min) usually delivered by the safety system of the NO delivery devices of the prior art.

By way of comparison, while the backup NO dosing system 200 integrated into the NO delivery device 1 of the invention makes it possible to guarantee an NO concentration substantially equal to the desired dosage, with a backup system based on a fixed flow rate of 250 ml/min, as conventionally used in the NO delivery devices of the prior art:

- for an average NO flow rate of 0.05 l/min necessary for normally ensuring an NO concentration of 10 ppmv (as used in neonatology with an HFO ventilator), the concentration resulting with the fixed flow rate of 250 ml/min is 50 ppmv, which corresponds to a fivefold multiplication of the desired dosage.
- conversely, for an average NO flow rate of 1 l/min necessary for ensuring 80 ppmv of NO concentration (as used in adults, for example in the case of pulmonary hypertension during heart surgery), the resulting concentration drops to 20 ppmv, which corresponds to a 75% decrease in the desired dosage.

In both cases, the considerable departures from the dosage can bring about situations that are unacceptable and dangerous for the patient, in contrast to the backup NO dosing system 200 integrated into the NO delivery device 1 of the invention, which makes it possible to comply with the desired dosage.

In other words, the backup NO dosing system 200 of the invention has undeniable advantages by increasing patient safety by:

- automatically injecting a backup NO flow rate without waiting for the user to recognize the situation and intervene by switching to the backup pneumatic dosing.
- guaranteeing that the NO concentration inhaled by the patient is similar to the concentration desired by the physician, that is, the desired dosage.

Of course, the switch-over to the backup NO dosing system 200 of the invention is only temporary, that is, it lasts only for the time needed to replace the faulty equipment or component that triggered the audible and/or visual alarm alerting the medical staff.

In order to avoid erroneous activation of the backup NO dosing system 200, the operating unit 130 is further configured to carry out suitable start-up and shut-down sequences. For example, if the NO therapy is deliberately stopped by the user, the operating unit 130 can command the actuator 203 in order to close the calibrated orifice 204. In the event of a deliberate shut-down and therefore the opening of the solenoid valve 202, the "closed" configuration of the calibrated orifice 204 thus then prohibits any circulation of NO flow in the backup line 201, while the NO delivery device 1 is shut down.

In general, according to the invention, in the event of the failure of the flow rate sensor 100 measuring the gas flow rate issuing from the mechanical ventilator 2 accompanied by the loss of the measurement signal, for example in the event of the disconnection of the upstream 103 and/or downstream 102 pressure measurement lines connected to the flow rate measurement module 100-1 of the flow rate sensor 100, the operating unit 130 retains its ability to command the actuators of the NO delivery device 1.

In this case, the operating unit 130 can detect the loss of signal from the flow rate sensor 100 and then immediately "activate" the backup dosing system 200 by stopping the operation of the proportional solenoid valve 113 and the solenoid valve 202 so that the proportional solenoid valve 113 switches to an idle position, that is a closed position, and the solenoid valve 202 of the backup line 201 simultaneously switches to its idle position, namely an open position permitting the circulation of the gas coming from the NO source in the backup line 201 and through the flow rate control device 210, which then delivers the NO/N2 flow at the pre-regulated flow rate, as explained above.

The flow of NO/N2 mixture can then follow the backup line 201 at the flow rate pre-set by the flow rate control device, for example a calibrated orifice or similar, before any loss of signal due to a malfunction, namely the backup flow rate determined by the operating unit 130 on the basis of the last respiratory gas flow rate measurement obtained before the malfunction and on the basis of the desired dosage, that is, the desired NO content after the NO/N2 flow has been mixed with the respiratory gas coming from the ventilator 2, such as air or an N2/O2 mixture, said mixing taking place in the inhalation branch 31 in the NO injection module 110, so as to obtain the final mixture to be administered to the patient containing the desired NO dosage, typically between 1 and 80 ppmv, for example of the order of 10 to 20 ppmv.

In other words, the NO/N2 flow coming from the backup line 201 will then join the injection line 111 (at 111*b*) in order to be injected into the inhalation branch 31 of the patient circuit 3 via the NO injection module 110, and mix therein with the respiratory gas flow, such as air or a nitrogen/oxygen mixture, containing oxygen, typically approximately at least 21% by volume of oxygen, coming from the ventilator 2, as already explained.

Of course, such a situation in which the operating unit 130 detects a loss of signal from the flow rate sensor 100, can be resolved and then return to normal, for example when the user reconnects the upstream 103 and/or downstream 102 pressure measurement lines of said flow rate sensor 100, if it/they has/have been unintentionally disconnected so as to cause the malfunction and the loss of signal.

Next, when the operating unit 130 determines that the signal from the flow rate sensor 100 is valid again, i.e. reception of the signal is restored, it can return to a normal operating state of the NO delivery device 1, that is by commanding the solenoid valve 202 back to a closed position in order to isolate the backup dosing system 200 from the injection line 111, and by commanding the proportional solenoid valve 113 again in order to deliver the NO flow rate that must be injected into the injection line 111 and the NO injection module 110 in order to satisfy the desired concentration of NO in the gas supplied to the patient.

Similarly, although this occurrence is rarer, the operating unit 130 can also determine that an internal failure of the NO flow rate sensor 112 has occurred, such as the breakage of its power supply cable, caused by vibrations during patient transport, for example.

In this case, the operating unit 130 is configured to operate in an identical way to the preceding case resulting from a loss of signal from the flow rate sensor 100 due to the accidental disconnection of the upstream 103 and/or downstream 102 lines, in order to activate the backup dosing system 200. However, such an internal failure of the sensor 112 is generally permanent and irreversible, and therefore requires technical intervention to replace the damaged, i.e. malfunctioning, elements.

The NO delivery device 1 provided with a backup NO dosing system 200 of the invention is particularly suitable for supplying a gas mixture comprising 1 to 80 ppmv of NO (dosage) and at least 21% by volume of oxygen to patients (adults, children, adolescents or newborns) suffering from pulmonary hypertension and/or hypoxia, which can cause pulmonary vasoconstriction or similar, for example caused by pulmonary diseases or disorders such as PPHN (persistent pulmonary hypertension of the newborn) or ARDS (acute respiratory distress syndrome), or those caused by heart surgery with placement of the patient on extracorporeal circulation.

What is claimed is:

1. An installation for supplying gas to a patient, comprising:

an NO delivery device configured to supply an $NO/N_2$ gas mixture, comprising:

an NO injection line configured to convey the $NO/N_2$ gas mixture, a valve device arranged on the injection line in order to control circulation of the $NO/N_2$ gas mixture in the injection line, a backup line connected fluidly to the injection line upstream and downstream of the valve device, said backup line comprising a backup solenoid valve and a flow rate control device, and a controller configured to interact with the backup solenoid valve, the flow rate control device and the valve device, a medical ventilator configured to supply a respiratory gas containing oxygen, a patient circuit to which the NO delivery device and the medical ventilator are fluidly connected in order to supply said patient circuit with said $NO/N_2$ gas mixture and with said respiratory gas containing oxygen, and a flow rate sensor configured to supply to the controller of the NO delivery device at least one measurement signal representing at least one gas flow rate within the patient circuit, wherein, in the event of interruption of reception, by the controller of the NO delivery device, of said at least one measurement signal supplied by the flow rate sensor:

the backup solenoid valve is configured to switch to an open position in order to allow the circulation of the $NO/N_2$ gas mixture in the backup line, the valve device is configured to switch to a closed position in order to stop any circulation of gas in the injection line, and the flow rate control device is configured to supply the $NO/N_2$ gas mixture at a pre-set backup gas flow rate, where said backup gas flow rate is determined by the controller based on at least one measurement signal supplied by the flow rate sensor, before said interruption of reception of said at least one measurement signal, and pre-regulated by a command to the flow rate control device from said controller, before said interruption of reception of said at least one measurement signal.

2. The installation according to claim 1, wherein the flow rate sensor is arranged on the patient circuit.

3. The installation according to claim 1, wherein the flow rate sensor is a mass flow sensor or a differential pressure measurement sensor.

4. The installation according to claim 1, wherein the flow rate sensor is of the type that measures differential pressure, comprising a measurement module traversed by an internal gas passage comprising an internal restriction, an upstream line and a downstream line for measuring pressure being fluidly connected to the measurement module of the flow rate sensor so as to make it possible to measure the pressure upstream and downstream of the internal restriction.

5. The installation according to claim 4, wherein a differential pressure sensor is connected to the flow rate sensor the upstream and downstream pressure measurement lines, said differential pressure sensor being arranged in the NO delivery device and interacting with the controller in order to supply them with pressure values measured by the flow rate sensor.

6. The installation according to claim 1, wherein the controller is configured to determine the backup gas flow rate based on at least one measurement signal supplied by the flow rate sensor, before said interruption of reception of said at least one measurement signal, and based on a desired final NO concentration.

7. The installation according to claim 1, wherein the backup gas flow rate is determined based on an average gas flow rate calculated based on a plurality of gas flow rates measured by the flow rate sensor in a given duration, before said interruption of reception of said at least one measurement signal.

8. The installation according to claim 1, wherein the given duration is between several seconds and several tens of seconds.

9. The installation according to claim 1, wherein the valve device comprises a proportional solenoid valve.

10. The installation according to claim 1, wherein the controller is configured to determine a backup flow rate based on at least one respiratory gas flow rate measured by the flow rate sensor, before the interruption of reception of said at least one measurement signal, and based on a final NO concentration to be obtained after mixing of the $NO/N_2$ mixture coming from the NO delivery device and the flow of respiratory gas containing oxygen coming from the ventilator.

11. The installation according to claim 1, wherein the flow rate control device comprises a proportional calibrated orifice system commanded by the controller to regulate the pre-set backup gas flow rate.

12. The installation according to claim 1, wherein the controller of the NO delivery device comprises at least one microprocessor.

13. The installation according to claim 1, wherein the valve device of the NO delivery device is configured so that it is normally in a closed position corresponding to an idle state, preventing any circulation of gas in the injection line.

14. The installation according to claim 1, wherein the backup solenoid valve of the NO delivery device is configured so that it is normally in an open position corresponding to an idle state, allowing the circulation of gas in the backup line.

15. The installation according to claim 1, wherein in the event of a loss of said at least one measurement signal, the controller is configured to stop operating the valve device and the backup solenoid valve of the NO delivery device, which then automatically switch to their idle state.

16. The installation according to claim 1, wherein the controller of the NO delivery device is further configured to, prior to any interruption of the reception or loss of the at least one measurement signal coming from the flow rate sensor, act on a proportional calibrated orifice system of the flow rate control device of the backup line in order to pre-regulate the desired backup gas flow rate.

17. The installation according to claim 1, wherein the respiratory gas containing oxygen is air or an oxygen/nitrogen mixture.

* * * * *